United States Patent [19]

Varaprath

[11] Patent Number: 4,933,413
[45] Date of Patent: Jun. 12, 1990

[54] PROCESS FOR SYNTHESIS OF ACYLAMINO ORGANOSILICON COMPOUNDS

[75] Inventor: Sudarsanan Varaprath, Midland, Mich.

[73] Assignee: Dow Corning Corporation, Midland, Mich.

[21] Appl. No.: 335,308

[22] Filed: Apr. 10, 1989

[51] Int. Cl.$^5$ ............................................. C08G 77/04
[52] U.S. Cl. .................................... 528/26; 524/858; 524/860; 524/869; 524/792; 524/755; 524/773; 528/10; 528/34; 528/37; 556/419
[58] Field of Search ................... 556/419; 528/10, 26, 528/34, 37; 524/858, 860, 869, 792, 755, 773

[56] References Cited

U.S. PATENT DOCUMENTS

| | | | |
|---|---|---|---|
| 2,929,829 | 3/1960 | Morehouse | 260/448.2 |
| 4,152,346 | 5/1979 | Seiler et al. | 260/448.8 |
| 4,507,455 | 3/1985 | Tangney et al. | 528/26 |
| 4,608,270 | 8/1986 | Varaprath | 528/26 |
| 4,788,310 | 11/1988 | Stein et al. | 556/419 |
| 4,861,906 | 8/1989 | Varaprath et al. | 556/419 |
| 4,861,907 | 8/1989 | Wright et al. | 556/419 |

FOREIGN PATENT DOCUMENTS 51-108022 9/1977 Japan .
56-74113 11/1979 Japan .

*Primary Examiner*—Melvyn I. Marquis
*Attorney, Agent, or Firm*—Killworth, Gottman, Hagan & Schaeff

[57] ABSTRACT

Organosilicon compounds containing at least one acylamino-substituted hydrocarbon radical are prepared by reacting an organohydroxysilicon compound containing at least one silicon-bonded hydroxy radical with a base to yield a silanolate. The silanolate is reacted with a cyclic aminosilane compound to form a siloxyalkylamide that is then reacted with an acyl chloride to give the desired product. All reactions can be carried out in a single reaction vessel using a nonaqueous solvent.

18 Claims, No Drawings

PROCESS FOR SYNTHESIS OF ACYLAMINO ORGANOSILICON COMPOUNDS

BACKGROUND OF THE INVENTION

This invention relates generally to a method for preparing organosilicon compounds that contain silicon-bonded acylamino-substituted hydrocarbon radicals. More specifically, the method involves the reaction of hydroxy silicon compounds with a base, a cyclic silyamine and an acyl halide in nonaqueous media.

Organosilicon compounds that contain silicon-bonded acylamino-substituted hydrocarbon radicals are well known and have been described in U.S. Pat. No. 4,608,270 to Varaprath, which is herein incorporated by reference.

As mentioned in Varaprath U.S. Pat. No. 4,608,270 and as taught in U.S. Pat. No. 2,929,829 to Morehouse, Japan 51/108022 to Furuya et al., Japan 56/74113 to Takamizawa, and West German DE 2365272 to Koetzsch et al., acylaminoorganopolysiloxanes can be synthesized by reacting aminosiloxanes with the corresponding acid chloride in the presence of a tertiary amine such as triethylamine. However, such a synthesis has several disadvantages. First, the removal of the voluminous precipitate of triethylamine hydrochloride by filtration is tedious. Second, a small amount of HCl is liberated even when an excess of amine is used. This HCl is detrimental to the stability of the polymer especially when the acid chloride has other reactive vinyl functionality such as where the acid chloride is methacrylyl chloride.

An alternative method for the preparation of acylaminoorganopolysiloxanes involves the reaction of aminosiloxanes and silanes with an acid anhydride or ester at elevated temperature. This is taught in U.S. Pat. No. 4,507,455 to Tangney and Ziemelis, assigned to the assignee of the present invention. Unfortunately at the elevated temperatures of the reaction, acrylamide derivatives undergo Michael addition and amidation of the acrylic double bond resulting in unwanted by-products and crosslinkage of the desired product which ultimately causes the polymer to gel.

Finally as taught in the above-mentioned U.S. Pat. No. 4,608,270 to Varaprath, these problems can be overcome by reacting the aminosilanes and siloxanes with acid chlorides in the presence of aqueous sodium hydroxide. The HCl that is produced on addition of acyl chloride is neutralized by hydroxide in the aqueous phase. However, a problem arises from the fact that this reaction is carried out in a two-phase system in which the aminosiloxane is dissolved in an organic solvent that is immiscible with water. Because the amide function is generally highly polar and hydrophilic, it has a tendency to absorb moisture. Incorporation of these units into the siloxane backbone increases water miscibility causing the polymers to emulsify easily thus making phase separation difficult.

To some extent this problem can be overcome by using chlorinated solvents such as methylene chloride or chloroform. However, when larger amounts of amide functionality or more resinous structure or both are used, it is cumbersome to prepare such compounds using a two-phase system even when chlorinated solvents are used.

Accordingly, the need remains for an improved method for preparing acylamino organosilicon compounds that avoids the phase separation and solvent toxicity problems previously encountered. The need also remains for an expanded method that permits use of silane starting materials having hydrolytically unstable groups such as $SiOCH_3$.

BRIEF SUMMARY OF THE INVENTION

These needs are met by the present invention which is directed to a method for preparing organosilicon compounds that contain at least one silicon-bonded, acylamino-substituted hydrocarbon radical by reacting a silanol, i.e., a hydroxy silicon compound, with a base followed by reactions with a cyclic silylamine and then an acyl halide. Preferably the preparation of the silicon-bonded acylamide product takes place according to the following scheme:

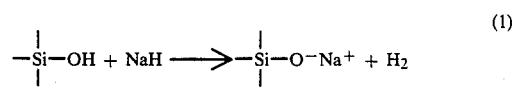

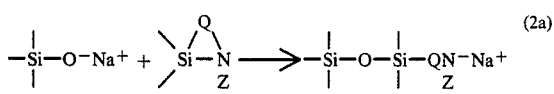

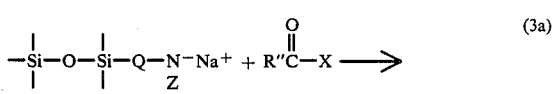

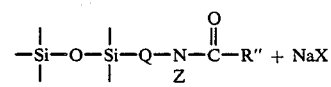

where, preferably, a hydroxysilicon compound, that is, a silicon compound having at least one silicon-bonded hydroxy radical, is reacted with a suitable base such as sodium hydride to liberate hydrogen (1). The resulting sodium silanolate is then reacted with a cyclic aminosilane compound to effect the cleavage of the silicon-nitrogen bond of the cyclic amine (2a). The resulting siloxyalkylamide anion is then reacted with an acyl choride to give the desired product (3a).

Other forms of the cyclic silazane may also be used, such as:

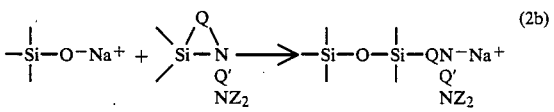

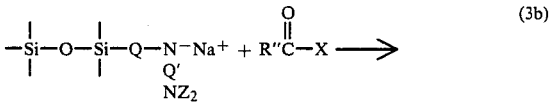

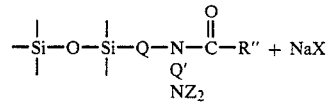

or

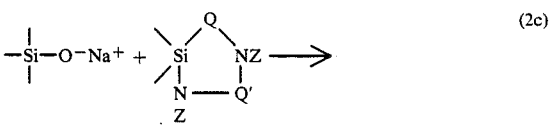

-continued

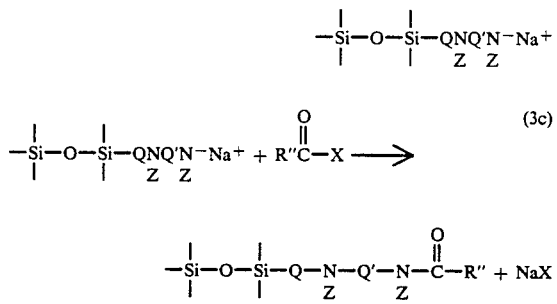

The hydroxysilicon compound can have any structure so long as it contains at least one silicon atom bonded to a hydroxy group. The other silicon bonds are satisfied by organic radicals or by divalent, silicon-linking oxygen atoms. Thus the hydroxy silicon compound can be a silane, siloxane, a silcarbane, or a silcarbanesiloxane.

In the above given schemes, Q denotes a divalent radical, Q' denotes a divalent hydrocarbon radical, Z denotes a hydrogen atom or a monovalent hydrocarbon radical, R" is a substituted or unsubstituted monovalent hydrocarbon radical, X is a halogen atom, and the open silicon valances are to be satisfied with organic radicals as noted below.

Preferably the reactions in the reaction schemes noted above are carried out in a single reaction vessel using a nonaqueous solvent such as toluene without isolation of intermediates. The reactions are homogeneous until the acyl halide addition which results in the precipitation of a metal halide such as sodium chloride. The metal halide is filtered off to obtain the acylamide as a toluene solution.

These reactions can all be carried out at room temperature if the acyl halide and/or the base is of the proper type, as delineated below. Otherwise the addition of the acrylyl halide is preferably carried out at low temperature to minimize the formation of by-products.

The reactions and work-up are straight forward. A one-phase system is used and only one reaction vessel required. The metal halide by-product can be easily removed by filtration. The use of nonaqueous solvents allows the use of organosilicon compounds with hydrolytically unstable functional groups such as the methoxy group. Likewise, because no separate aqueous phase is used, there are no phase separation problems. In addition, because chlorinated solvents are not needed for phase separation purposes, no toxicity problems are encountered.

Thus an improved process without many of the drawbacks of the prior art is provided for producing acyl-amino organosilicon compounds. As described in the Varaprath Pat. No. U.S. 4,608,270, the acylamino organosilicon products are useful for paper release coatings and coupling agents. They are also useful as photoresists in microlithography and as conformal coatings, for example, as moisture and radiation dual cure coatings of the type disclosed in copending applications Ser. Nos. 118,086 filed on Nov. 6, 1987 now U.S. Pat. No. 4,824,875 and 200,827 filed June 1, 1988.

Accordingly, it is an object of the present invention to provide an improved method for preparing organosilicon compounds that contain silicon-bonded acylamino-substituted hydrocarbon radicals of the type described in the Varaprath Pat. No. 4,608,270. These and other objects of and advantages of the invention will become apparent from the following description and the appended claims.

DETAILED DESCRIPTION OF THE PREFERRED EMBODIMENTS

The preferred method consists of reacting a base with a silanol having at least one silicon-bonded hydroxy radical. The remaining silicon bonds are satisfied with organic radicals or divalent, silicon-linking, oxygen atoms, or both. The resulting silanolate anion is reacted with a cyclic silylamine which undergoes cleavage at the silicon nitrogen bond with addition to the silanolate anion to give a siloxyalkylamide anion. An acyl halide is then reacted with the amide anion to give the desired product. The reaction is carried out in a non-aqueous solvent.

Preferably alkali-metal hydride is added to a hydroxysilicon compound that has been dissolved in a nonaqueous solvent. After the liberation of hydrogen is complete, a cyclic silylamine is added to the reaction mixture followed by the addition of an acyl halide. The alkali-metal halide that precipitates on addition of the acyl chloride is removed by filtration to give a nonaqueous solution of the desired product.

When the base is NaH or KH and the acyl halide is not an acrylyl halide the entire reaction scheme can be carried out at room temperature. When the base is LiAlH$_4$, n-BuLi or a Grignard Reagent low temperature ($-20°$ to $0°$ C.) must be employed to avoid siloxane bond cleavage, regardless of the type of acyl halide used.

The silanol that is to be reacted with the base can have any structure as long as it contains at least one silicon atom bonded to a hydroxy radical. The other silicon bonds are satisfied by organic radicals other than the hydroxy radicals noted above or by divalent, silicon-linking oxygen atoms. Thus the hydroxysilicon compound can be a silane, a siloxane, a silcarbane, or a silcarbanesiloxane.

Silicon-bonded radicals, other than the above-noted hydroxy radical, include organic radicals and divalent, silicon-linking, oxygen atoms. Examples of organic radicals include, but are not limited to, divalent, silicon-linking hydrocarbon radicals such as the Q and Q' radicals noted below, and halogenated derivatives thereof, monovalent hydrocarbon radicals such as the R radicals noted below, and halogenated derivatives thereof, alkoxy radicals such as methoxy radicals, hydroxy radicals, —OAr radicals (where Ar is an aryl group), and hydrogen atoms. Preferably said organic radicals contain no more than 6 carbon atoms, such as methyl, 3,3,3-trifluoropropyl, phenyl and vinyl radicals, and most preferably are methyl radicals.

The silanols used in the process of this invention are preferably silanes or siloxanes having the average formula R'$_c$(OH)$_d$SiO$_{(4-c-d)/2}$ where R' denotes an R radical or a substituted R radical, "c" denotes a number having a value of from 0 to 3, such as 0, 0.5, 1.01, 2, 2.1, and 3, "d" denotes a number having a value of from >0 to 4, such as 0.01, 0.5, and 1, 2, and 3 and "c"+"d" has a value of less than or equal to 4 such as 1.5, 1.99, 2.01, 3, and 3 and 4. Of course, the hydroxysilicon compound must contain an average of at least one silicon-bonded, hydroxy radical per molecule. The hydroxysilicon compound can contain siloxane units that are free of hydroxy radicals such as R'$_c$SiO$_{(4-c)/2}$ such as MeSiO$_{3/2}$, Me$_2$SiO$_{2/2}$, Me$_3$SiO$_{1/2}$, MeViSiO$_{2/2}$, Me$_2$(OAr)SiO$_{1/2}$, ViMe$_2$SiO$_{1/2}$, and SiO$_{4/2}$ units, in addition to siloxane units that contain the required hydroxy radicals. Herein the symbols Me, Ph, Vi, and Ar denote methyl, phenyl, vinyl, and aryl, respectively.

Hydroxysilanes have the formula R'$_e$Si(OH)$_{4-e}$ where "e" denotes a number having a value of 0, 1, 2, or 3, such as Ph$_3$SiOH and Ph$_2$Si(OH)$_2$. Hydroxysiloxanes can have any structure, such as linear siloxanes having the formula YR'$_2$SiO(R$_2$SiO)$_x$(YR'SiO)$_y$SiR'$_2$Y; cyclic or branched structures such as (YRR'SiO)$_4$Si, (YRR'SiO)$_3$SiY and (YR'SiO)$_4$; and resinous structures such as Y$_a$SiO$_{(4-a)/2}$; where each Y denotes, independently, an R' radical or a hydroxy radical, at least one Y being a hydroxy group, and "x" and "y" denote numbers having average values of from 0 to 5000 and 0 to 500, respectively, and "a" denotes a number having an average value of less than 2.

Examples of hydroxysiloxanes include, but are not limited to, HOMe$_2$SiO(Me$_2$SiO)$_{2000}$SiMe$_2$OH, (HOMe$_2$SiO)$_4$Si, HOMe$_2$SiO(Me$_2$SiO)$_3$(PhMeSiO)$_1$SiMe$_2$OH, Me$_3$SiO(MeOHSiO)$_1$SiMe$_3$, HOMePhSiO(MePhSiO)$_5$SiMePhOH, HOMe$_2$SiO(MeOHSiO)$_1$SiMe$_2$OH, HOMe$_2$SiO(Me$_2$SiO)$_{20}$SiMe$_2$OH, Ph$_{0.5}$(OH)$_{0.1}$Me$_{0.5}$SiO$_{1.45}$ and HOMeViSiO(MeViSiO)$_8$SiMeViOH. Silanols (hydroxysilicon compounds) and their preparation are well known in the organosilicon art. Some are commercially available.

The base is any base capable of removing a proton from the hydroxy group of the hydroxysilicon compound, i.e., any reagent that is capable of forming a silanolate from a silanol, e.g., sodium, potassium or lithium aluminum hydride, a Grignard reagent or n-butyl lithium. Preferably sodium hydride is used with linear and network resins containing phenyl or phenyl methyl siloxanes. Preferably n-butyl lithium is used with linear methyl siloxanes although other bases such as potassium hydride, lithium aluminum hydride or a Grignard reagent may be used.

The cyclic silazane may have the formula

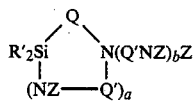

where R' denotes a substituted or unsubstituted monovalent hydrocarbon radical, Q and Q' denote divalent hydrocarbon radicals, Z denotes a hydrogen atom or a monovalent hydrocarbon radical, i.e., an R radical, and "a" is equal to 0 or 1, "b" is equal to 0 or 1, and "a"+"b" is equal to 0 or 1.

Examples of Q radicals and Q' radicals include, but are not limited to, alkylene radicals such as methylene, ethylene, propylene, isopropylene, butylene, isobutylene, hexylene, octylene, and arylene radicals such as phenylene, tolylene and xylylene. The Q radical may also contain a silicon atom that is bonded to the cyclic nitrogen without silicon linkage. Q is preferably ethylene and Q' is preferably propylene or isobutylene.

Examples of Z hydrocarbon radicals (R radicals) include, but are not limited to, alkyl radicals such as methyl, ethyl, propyl, butyl, hexyl, and octyl; cycloaliphatic radicals such as cyclohexyl; aryl radicals such as phenyl, benzyl, styryl, tolyl, and xenyl; and alkenyl radicals such as vinyl and allyl.

Thus, examples of cyclic silazanes include, but are not limited to,

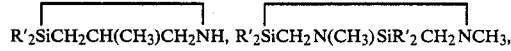

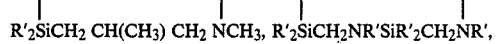

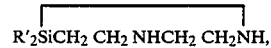

R'$_2$SiCH$_2$CH$_2$CH$_2$NCH$_2$CH(CH$_3$)CH$_2$NH$_2$, and

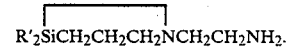

Cyclic aminosilicon compounds and their preparation are also well known in the organosilicon art. Some are commercially available. The disclosure of U.S. Pat. No. 3,146,250 is incorporated herein by reference to further teach how to prepare cyclic silazanes that can be used in the method of this invention.

The acyl halide can have any structure such as a linear, branched, or cyclic structure having aromatic, heterocyclic, olefinic or paraffinic bonding and containing one or more carbon-bonded —COX radicals, where X denotes a halogen atom. Preferably the acyl halide has the structure R"COX where X denotes a halogen atom such as Cl, Br, or I but preferably chlorine, and R" denotes a substituted or unsubstituted monovalent hydrocarbon radical.

Examples of unsubstituted R" radicals include, but are not limited to, those delineated above for hydrocarbon radicals (R radicals). Examples of corresponding acyl halides include acetyl chloride, benzoyl chloride and, most preferably, acrylyl chloride, methacrylyl chloride, cinnamoyl chloride, styrenecryloyl chloride, and diphenylcyclopropenecarbonyl chloride.

Examples of substituted R" radicals include, but are not limited to, halogenated R radicals such as —CF$_3$ and —C$_6$H$_4$Cl, and other substituted radicals which are stable under the reaction conditions employed in the method of this invention such as —CH$_2$CH$_2$CN, —C$_6$H$_4$NO$_2$ and —C(CN)=CH$_2$.

A nonaqueous solvent is used for the various reactions of the reaction scheme. The solvent can be any suitable nonaqueous liquid that will not react with the components of the reaction. Preferably the solvent is a solvent for the organosilicon product of the reaction. Examples of suitable solvents include, but are not limited to, hydrocarbons such as toluene, xylene, hexane, cyclohexane and heptane; halogenated hydrocarbons such as methylene chloride, chloroform, trichloroethylene and trichloroethane; and oxygenated compounds such as ethyl ether and ethyl acetate. Mixtures of two or more solvents can also be used, it only being required that the mixture, and not necessarily all of the components in the mixture, be a solvent for all the starting materials. Preferably, a solvent such as toluene is used. The amount of solvent that is used should be sufficient to dissolve the starting materials and, preferably, the acylamino organosilicon product as well.

The necessary components of the reaction mixture, i.e., a nonaqueous solvent, the hydroxysilicon compound, the base, the cyclic aminosilicon compound, and the acyl halide are added according to the reaction scheme sequence given above. In a preferred embodiment, the base is added to a non-aqueous solution of the hydroxy silicon starting material and the reaction allowed to continue until the reaction goes to completion. Next, the cyclic amine is dissolved in the solvent and added to the reaction mixture so as to react with the product from the previous reaction, i.e., the silanolate anion. Finally, the acyl chloride is dissolved in the solvent and added to the reaction mixture so as to react with the product from the second reaction, i.e., the siloxyalkylamide anion.

A deficiency of acyl halide relative to the total number of reactive NH groups, although merely leading to the preparation of incompletely acylated product when the acyl halide is free of aliphatic unsaturation, leads to products which can undergo a Michael-Addition type reaction when the acyl halide contains aliphatic unsaturation. For this reason, it is preferred, although not required, to fully acrylate the aminosilicon compound when an acrylyl halide is used.

Except as noted above the method of this invention can be practiced at any reasonable temperature. Advantageously this method proceeds readily at room temperature; however, this method should be practiced at as low a temperature as possible to minimize the formation of byproducts when certain reactants, as noted above, are used. Accordingly, when using the method of this invention to prepare acrylyl-substituted aminosilicon compounds, the reaction should be conducted at a temperature of from $-10°$ to $10°$ C. Lower reaction temperature can be used provided the solvent does not freeze. Higher reaction temperatures substantially reduce the yield of desired product.

The usual low shear means such as stirrers, paddles, and impellers are sufficient to maintain sufficient agitation. Agitation is maintained until the acylation reaction is finished, typically within an hour.

After the reaction is finished, the product of the reaction can be separated from the metal chloride precipitate by filtration through celite or anhydrous $MgSO_4$. The solvent can be removed from the product using conventional means such as a rotary evaporator. When acrylyl-substituted products are to be separated from the solvent, it is desirable to add a polymerization inhibitor such as sodium nitrite to the solution prior to any separating action such as distilling or fractionation. The products of this method are useful as polar silicon-containing additives for cosmetic compositions, coating compositions, textile treating compositions, and paints. The compositions are useful as comonomers with polymerizable vinyl monomers such as styrene, butadiene, methyl methacrylate, ethyl acrylate, vinyl acetate, vinyl chloride, vinylidene chloride and acrylonitrile. In particular the compounds having acrylamide-substituted hydrocarbon radicals are useful as a reactive component in free radical curable compositions such as radiation curable compositions used for paper, resin protective, and optical fiber coatings. Compositions containing $C_6H_5$ $(CH)_4CON-$ and $(C_6H_5)_2C_3CON-$ functionalities are widely utilized in the semiconductor industry in photo resist, photodelineable coatings, and hybrid circuits.

The following examples are disclosed to further teach the practice of the invention and are not intended to limit the invention as it is delineated in the claims.

EXAMPLE 1

Ten (10.0) grams of hydroxy terminated poly(phenylmethylsiloxane) $\{HO(PhMeSiO)_xH$ where x is about 3$\}$ was placed in a 250 ml, 3-necked, round-bottom flask fitted with an addition funnel, $N_2$ inlet, and a magnetic sir bar. About 70 ml of dry toluene was added. The contents were degassed and saturated with nitrogen. Sodium hydride (0.70 g; 60% mineral oil solution) was added in small increments. The reaction began instantly as evidenced by brisk evolution of $H_2$ gas. A homogeneous solution was observed. After the addition was over, a cyclic silicon amine having the structure

$(CH_3)_2SiCH_2CH(CH_3)CH_2NCH_3$ and dissolved in 10 ml of toluene, was added dropwise with stirring. Once again a homogenous solution was observed. After the addition was over, the reaction flask was cooled in an ice bath and acrylyl chloride was added dropwise. The temperature of the reaction was maintained below $5°$ C. throughout the addition of the acrylyl chloride. At the end of the reaction, the fine suspension of NaCl that had formed was removed by filtration through celite or anhydrous $MgSO_4$. The removal of toluene (rotary evaporator) yielded 13.0 g (100% yield) of the acrylamide as a viscous fluid. An infrared absorption (neat) at 1630 cm$^{-1}$ indicated acrylamide. $^1$H NMR ($CDCl_3$) absorption between 5.4 and 6.1 ppm confirmed the presence of the vinyl group of acrylamide functionality.

EXAMPLE 2

The general procedure of Example 1 using 10.0 g of the hydrolyzate obtained from the co-hydrolysis of $PhSiCl_3$ and n-propylSiCl$_3$ in a ratio of 70:30 by weight, respectively, 0.70 g NaH, 2.52 g of the cyclic silicon amine as defined in Example 1 and 1.6 g of acrylyl chloride gave the acrylamide resin in almost quantitative yield.

EXAMPLE 3

The general procedure of Example 1 using 50.0 g of the resin hydrolyzate as defined in Example 2, 32.9 ml n-butyl lithium (2.6M in tetrahydrofuran (THF)), 12.6 g of the cyclic silicon amine as defined in Example 1 and 8.77 g of acrylyl chloride gave an acrylamide functional resin in 90% yield.

EXAMPLE 4

The general procedure of Example 1 using 50.0 g of the resin hydrolyzate as defined in Example 2, 19.6 ml isopropyl magnesium bromide (3.0M in THF), 8.41 g of the cyclic silicon amine as defined in Example 1 and 5.3 g of acrylyl chloride gave an acrylamide functional resin in 74.1% yield.

EXAMPLE 5

The general procedure of Example 1 using 10.0 g of the resin hydrolyzate as defined in Example 2, 4.70 g NaH (as 60% mineral oil), 2.52 g of the cyclic solution amine as defined in Example 1 and 2.94 g of cinnamoyl chloride gave the cinnamamide functional resin in quantitative yield.

EXAMPLE 6

The general procedure of Example 1 using 5.0 g of hydroxy terminated poly(dimethylsiloxane) of the structure HO(Me$_2$SiO)$_x$H where x is about 6, 0.8 g of potassium hydride, 1.1 g of the cyclic silazane as defined in Example 1 and 0.7 g of acrylyl chloride gave the corresponding acrylamide functional poly(dimethylsiloxane).

EXAMPLE 7

Using 5.0 g of the hydroxy terminated poly(dimethylsiloxane) as defined in Example 6, 5 ml of n-butyl lithium (1.55M in hexane), 1.1 g of cyclic silazane as defined in Example 1 and 0.7 g of acrylyl chloride gave the corresponding acrylamide functional polysiloxane in greater than 95% yield. The procedure outlined in Example 1 was followed except for the following modifications: The n-butyl lithium addition was performed at −20° C. followed by warming to 0° C. The addition of cyclic silazane was performed at 0° C. followed by the addition acrylyl chloride also at 0° C.

That which is claimed is:

1. A method for preparing an organosilicon compound containing at least one silicon-bonded acylamino-substituted hydrocarbon radical comprising:
   (1) reacting a hydroxysilicon compound having at least one silicon-bonded hydroxy radical, all other silicon valences therein being satisfied by radicals selected from the group consisting of organic radicals and divalent, silicon-linking, oxygen atoms with a base in a nonaqueous solvent to form a silanolate anion,
   (2) then reacting said silanolate anion with a cyclic aminosilicon compound in said nonaqueous solvent to give a siloxyalkylamide, and
   (3) then reacting said siloxyalkylamide with an acyl halide in said nonaqueous solvent to yield said acylamino organosilicon compound.

2. The method according to claim 1 wherein said hydroxysilicon compound has the average unit formula R'$_c$(OH)$_d$SiO$_{(4-c-d)/2}$ wherein
   R' denotes a monovalent substituted or unsubstituted hydrocarbon radical,
   "c" has a value of from 0 to 3,
   "d" has a value of >0 to 4, and
   "c"+"d" has a value of less than or equal to 4.

3. The method according to claim 2 wherein said hydroxysilicon compound is a siloxane have the formula YR'$_2$SiO(R$_2$SiO)$_x$(YR'SiO)$_y$SiR'$_2$Y wherein
   Y denotes R' or —OH,
   x has a value of from 0 to 5000, and
   y has a value of from 0 to 500.

4. The method according to claim 3 wherein said hydroxysilicon compound is a silane having the formula R'$_e$Si(OH)$_{4-e}$ wherein e has a value of 0, 1, 2, or 3.

5. The method according to claim 2 wherein R' is selected from the group consisting of methyl, phenyl and vinyl.

6. The method according to claim 1 wherein said cyclic aminosilicon compound has the formula

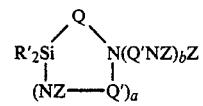

wherein
   R' denotes a substituted or unsubstituted hydrocarbon radical,
   Q denotes a divalent radical,
   Q' denotes a divalent hydrocarbon radical,
   Z denotes a hydrogen atom or a monovalent hydrocarbon radical,
   "a" is 0 or 1,
   "b" is 0 or 1, and
   "a"+"b" is 0 or 1.

7. A method according to claim 1 wherein said acyl halide is a compound selected from the group consisting of CH$_2$=CHCOCl, CH$_2$=C(CH$_3$)COCl, C$_6$H$_5$CH=CHCOCl, (C$_6$H$_5$)$_2$C$_3$HCOCl and C$_6$H$_5$CH=CH—CH=CHCOCl.

8. The method according to claim 1 wherein said reaction mixtures are continuously agitated.

9. The method according to claim 1 further comprising filtering said solution after said reaction with acyl halide to removed precipitated metal halide.

10. The method according to claim 1 wherein said reaction is carried out at a temperature of from about 0 to 10° C.

11. The method according to claim 7 wherein said reaction of said acyl halide is carried out at a temperature of from about 0° to 10° C.

12. The method according to claim 1 wherein said base is an alkali metal hydride.

13. The method according to claim 1 wherein said base is sodium hydride.

14. The method according to claim 1 wherein said base is a Grignard reagent.

15. The method according to claim 1 wherein said base is isopropyl magnesium bromide.

16. The method according to claim 1 wherein said base is n-butyl lithium.

17. The method according to claim 1 wherein said nonaqueous solvent is toluene.

18. The method according to claim 1 wherein the molar amount of said acyl halide is in about 10% molar excess over the molar amount of at least one nitrogen atom per molecule of said siloxamide.

* * * * *